(12) United States Patent
Baribault

(10) Patent No.: US 9,915,790 B2
(45) Date of Patent: Mar. 13, 2018

(54) FIBER INSPECTION MICROSCOPE AND POWER MEASUREMENT SYSTEM, FIBER INSPECTION TIP AND METHOD USING SAME

(71) Applicant: EXFO INC., Quebec (CA)

(72) Inventor: Robert Baribault, Quebec (CA)

(73) Assignee: EXFO INC., Quebec (CA)

( * ) Notice: Subject to any disclaimer, the term of this patent is extended or adjusted under 35 U.S.C. 154(b) by 168 days.

(21) Appl. No.: 14/962,301

(22) Filed: Dec. 8, 2015

(65) Prior Publication Data

US 2016/0170151 A1    Jun. 16, 2016

Related U.S. Application Data

(60) Provisional application No. 62/091,872, filed on Dec. 15, 2014, provisional application No. 62/154,018, filed on Apr. 28, 2015.

(51) Int. Cl.
   *G02B 6/38*     (2006.01)
   *G01N 21/952*   (2006.01)
   (Continued)

(52) U.S. Cl.
   CPC ............ *G02B 6/385* (2013.01); *G01M 11/30* (2013.01); *G01M 11/31* (2013.01);
   (Continued)

(58) Field of Classification Search
   CPC .... G01M 11/088; G01M 11/30; G01M 11/31; G01M 11/33; G01M 11/331;
   (Continued)

(56) References Cited

U.S. PATENT DOCUMENTS

| | | |
|---|---|---|
| 4,595,265 A | 6/1986 | Hodgson et al. |
| 5,127,725 A | 7/1992 | Mueller et al. |

(Continued)

FOREIGN PATENT DOCUMENTS

| | | |
|---|---|---|
| WO | 2011140352 A1 | 11/2011 |
| WO | 2013097041 A1 | 7/2013 |

OTHER PUBLICATIONS

AFL Global, "NOYES FOCIS Fiber Optic Connector Inspection System", 2012, AFL Global Website, U.S.A.

(Continued)

*Primary Examiner* — Gordon J Stock, Jr.
(74) *Attorney, Agent, or Firm* — Norton Rose Fulbright Canada LLP; Alexandre Daoust

(57) ABSTRACT

The fiber inspection microscope and power measurement system for inspecting an endface of an optical fiber at an angle-polished connector generally has: a mating interface for receiving the angle-polished connector, the endface causing a mean propagation direction of light exiting the optical fiber at endface to be tilted relative to an imaging path of the system; a converging element to be optically coupled to the endface and being configured to receive the tilted light and to redirect the tilted light toward the imaging path of the fiber inspection microscope system; and a power detection assembly optically coupled to the converging element, the power detection assembly being configured to detect an optical power associated with the tilted light redirected by the converging element.

18 Claims, 13 Drawing Sheets

(51) Int. Cl.
  *G01N 21/88* (2006.01)
  *G01M 11/00* (2006.01)
  *G02B 6/32* (2006.01)
  *G02B 6/42* (2006.01)
  *G01N 21/95* (2006.01)
  *G02B 21/00* (2006.01)

(52) U.S. Cl.
  CPC ....... *G01N 21/8803* (2013.01); *G01N 21/952* (2013.01); *G02B 6/32* (2013.01); *G02B 6/381* (2013.01); *G02B 6/423* (2013.01); *G02B 6/4292* (2013.01); *G02B 21/0016* (2013.01); *G01N 2021/9511* (2013.01)

(58) Field of Classification Search
  CPC ............. G01M 11/332; G01M 11/333; G01M 11/334; G01M 11/335; G01M 11/336; G01M 11/337; G01M 11/338; G02B 21/0016; G02B 6/32; G02B 6/381; G02B 6/385; G02B 6/423; G02B 6/4292; G01N 2021/9511; G01N 21/88; G01N 21/8803; G01N 21/8806; G01N 21/94; G01N 21/95; G01N 21/9515; G01N 21/942; G01N 21/958; G01N 21/952
  USPC ........................................................ 356/73.1
  See application file for complete search history.

(56) References Cited

U.S. PATENT DOCUMENTS

| | | | |
|---|---|---|---|
| 5,179,419 A | 1/1993 | Palmquist et al. | |
| 5,432,330 A | 7/1995 | Nakamura | |
| 5,459,564 A | 10/1995 | Chivers | |
| 5,724,127 A | 3/1998 | Csipkes et al. | |
| 6,466,366 B1 | 10/2002 | Dominique | |
| 6,636,298 B1 | 10/2003 | Bachelder et al. | |
| 6,751,017 B2 | 6/2004 | Cassady | |
| 6,793,399 B1 | 9/2004 | Nguyen | |
| 6,831,738 B2 | 12/2004 | Rogers et al. | |
| 6,879,429 B2 | 4/2005 | Wong et al. | |
| 6,879,439 B2 | 4/2005 | Cassady | |
| 6,989,895 B2 | 1/2006 | Buzzetti | |
| 7,012,686 B2 | 3/2006 | Rogers et al. | |
| 7,042,562 B2 | 5/2006 | Kiani et al. | |
| 7,162,073 B1 | 1/2007 | Akgul et al. | |
| 7,239,788 B2 | 7/2007 | Villeneuve | |
| 7,277,181 B2 | 10/2007 | Lin | |
| 7,312,859 B2 | 12/2007 | Koudelka et al. | |
| 7,336,884 B2 | 2/2008 | Zhou et al. | |
| 7,356,236 B1 | 4/2008 | Huang et al. | |
| 7,502,164 B2 | 3/2009 | Lytle et al. | |
| 7,566,176 B2 | 7/2009 | Lytle et al. | |
| 7,630,066 B2 | 12/2009 | Kachmar | |
| 7,663,740 B2* | 2/2010 | Lu | G01N 21/94 356/72 |
| 7,667,831 B2 | 2/2010 | Koudelka et al. | |
| 7,710,642 B2 | 5/2010 | Lytle et al. | |
| 8,164,744 B2 | 4/2012 | Narum et al. | |
| 8,908,167 B2 | 12/2014 | Flora et al. | |
| 8,976,345 B2 | 3/2015 | Zhou et al. | |
| 8,988,670 B2* | 3/2015 | Zhou | B08B 5/02 356/73.1 |
| 9,110,251 B2* | 8/2015 | Chen | G01N 21/958 |
| 2004/0101254 A1* | 5/2004 | Erdman | G02B 6/3871 385/78 |
| 2008/0278709 A1 | 11/2008 | Lu | |
| 2010/0141934 A1 | 6/2010 | Narum et al. | |
| 2011/0292198 A1 | 12/2011 | Lapstun et al. | |
| 2014/0354977 A1 | 12/2014 | Zhou et al. | |
| 2015/0092043 A1* | 4/2015 | Baribault | H04N 5/2252 348/125 |

OTHER PUBLICATIONS

JDSU Uniphase Corporation, "HP2 Series Fiber Inspection and Test System with 3.5-inch Video Display", Mar. 2010, JDSU Website, pp. 1-4, U.S.A.

* cited by examiner

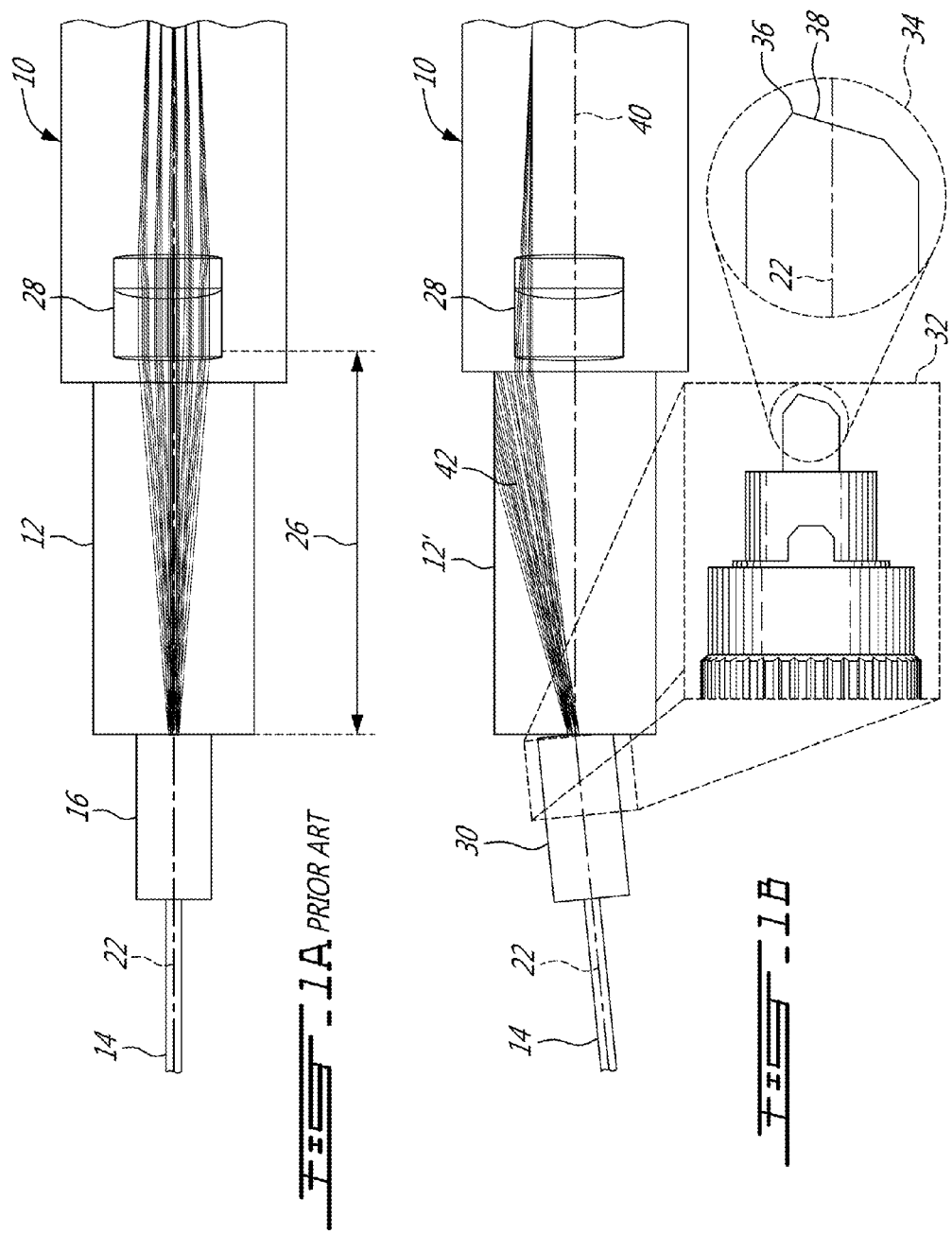

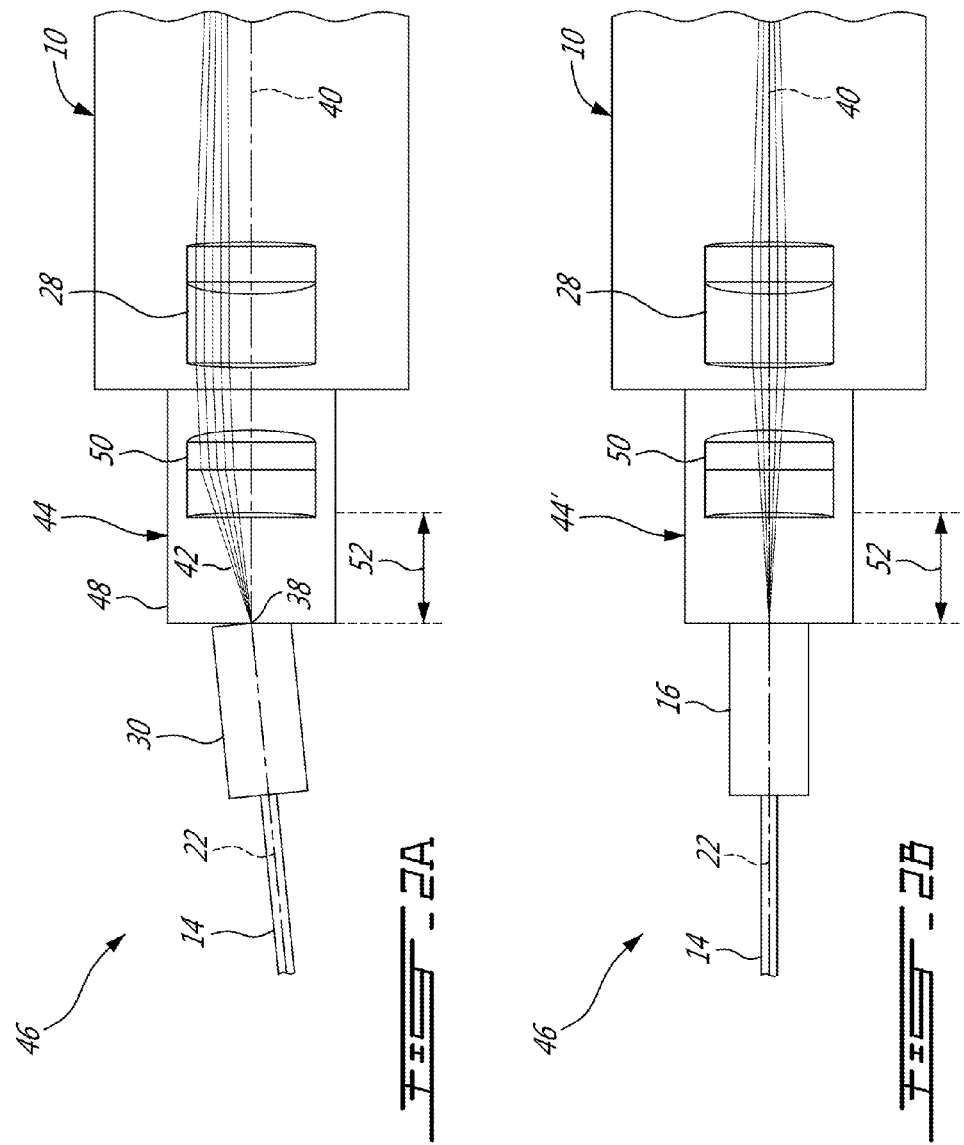

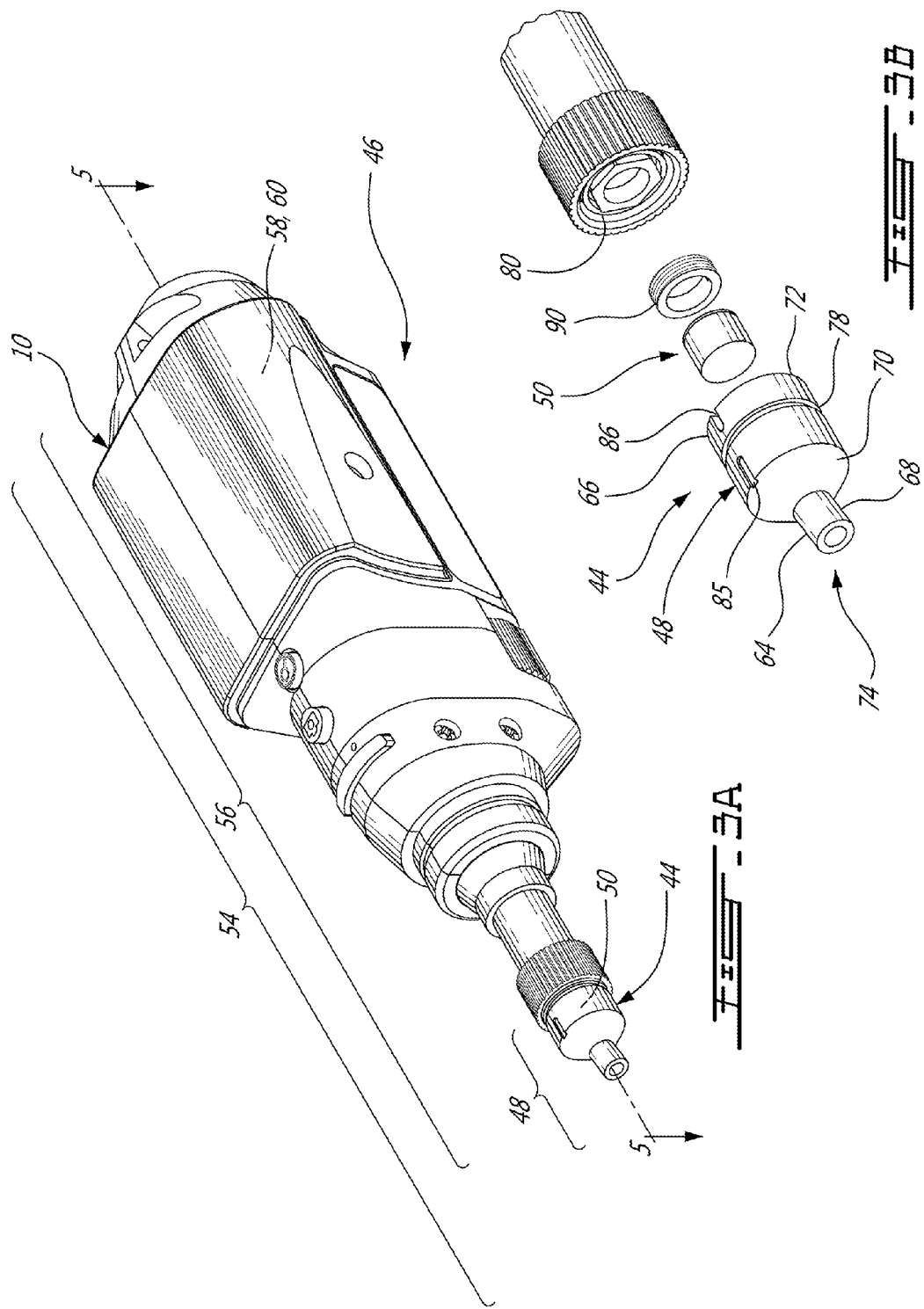

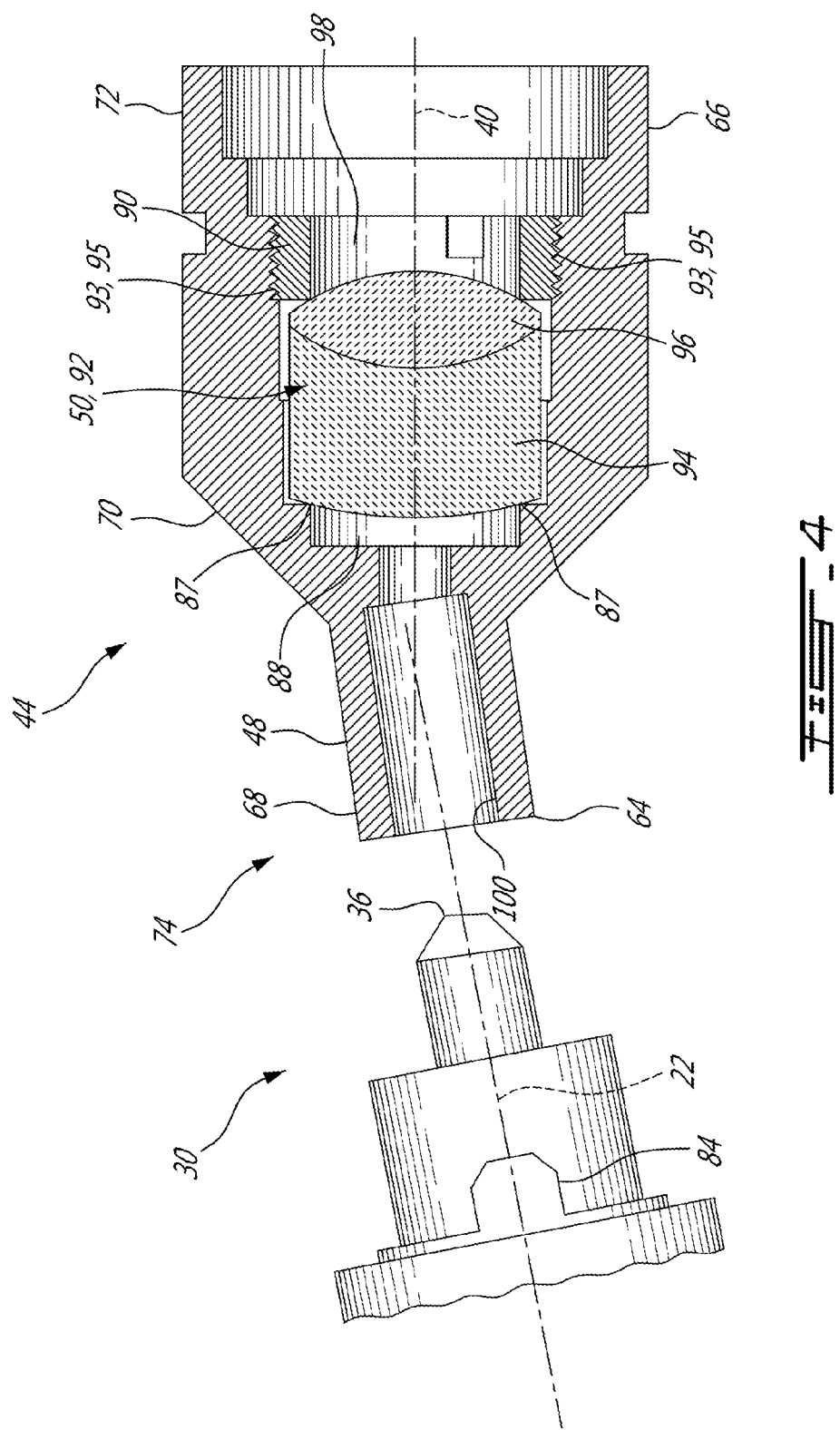

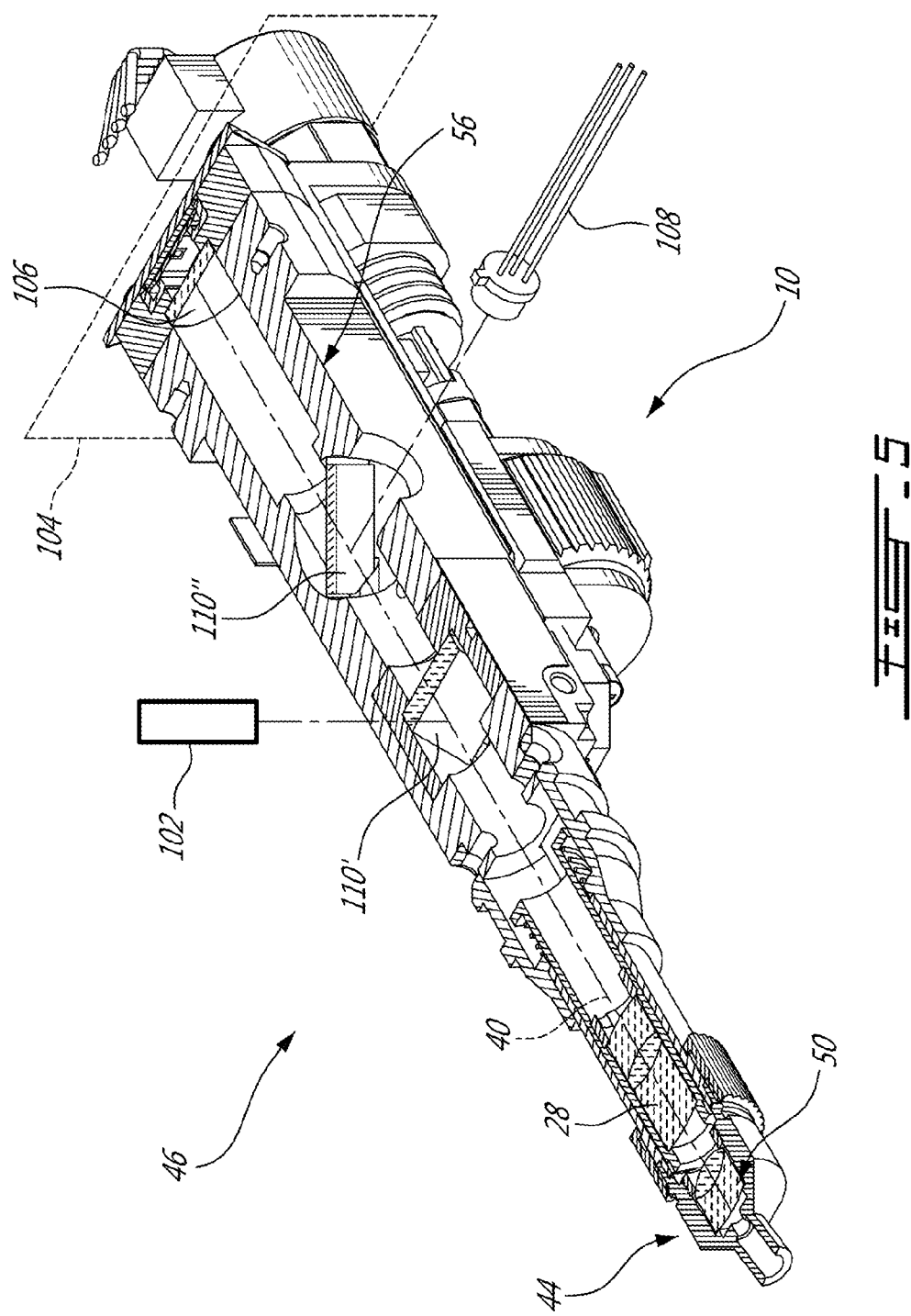

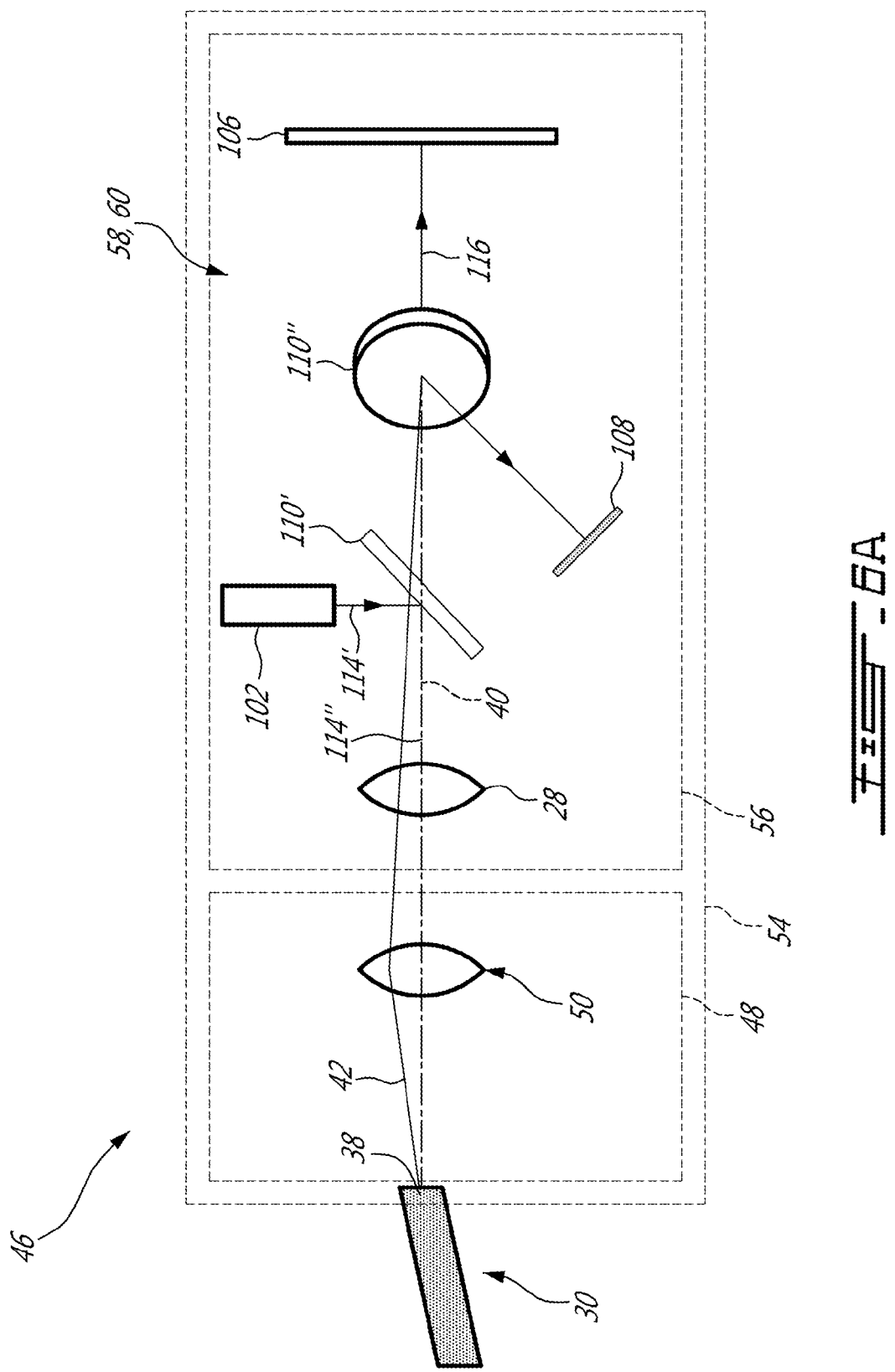

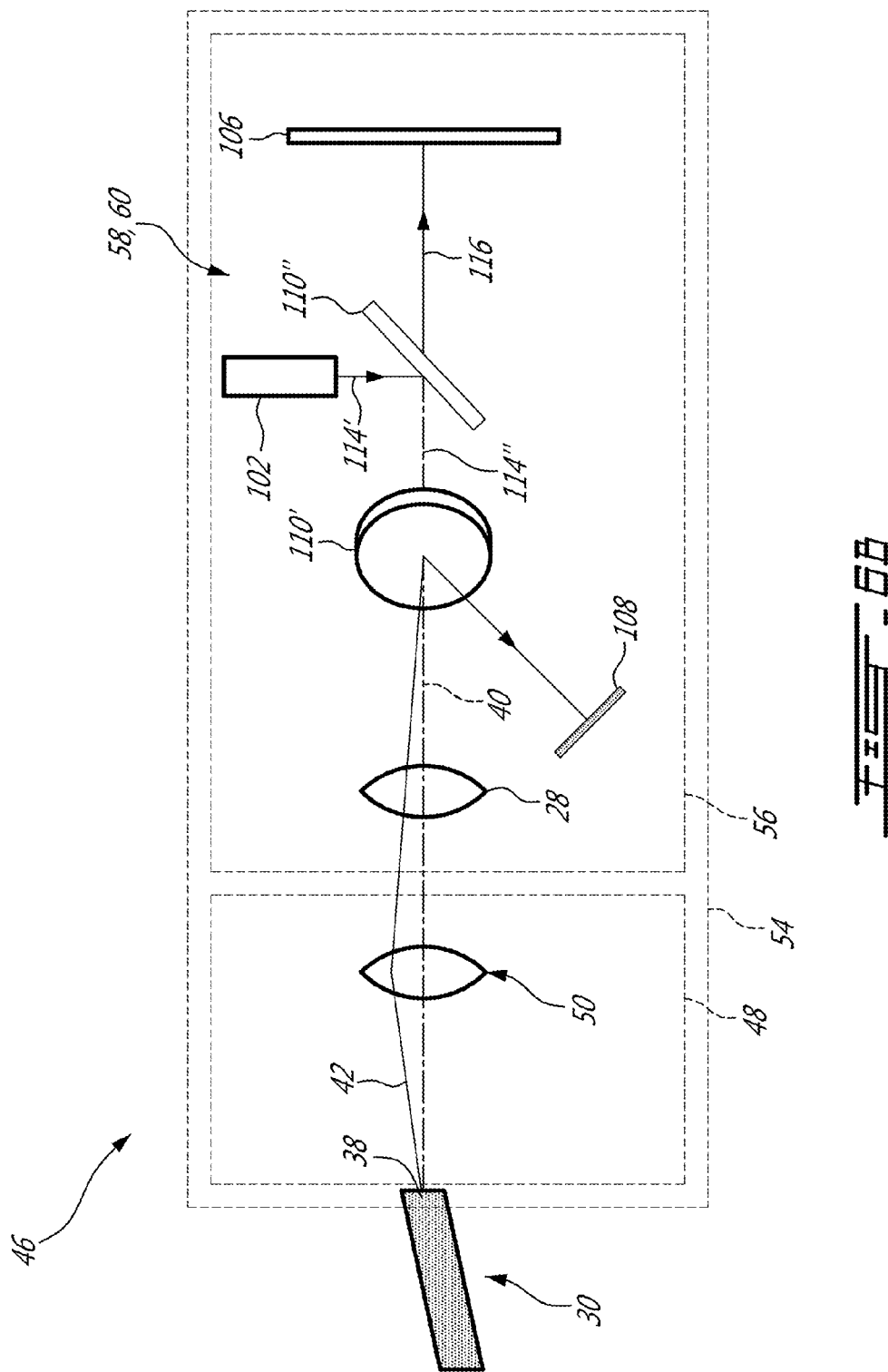

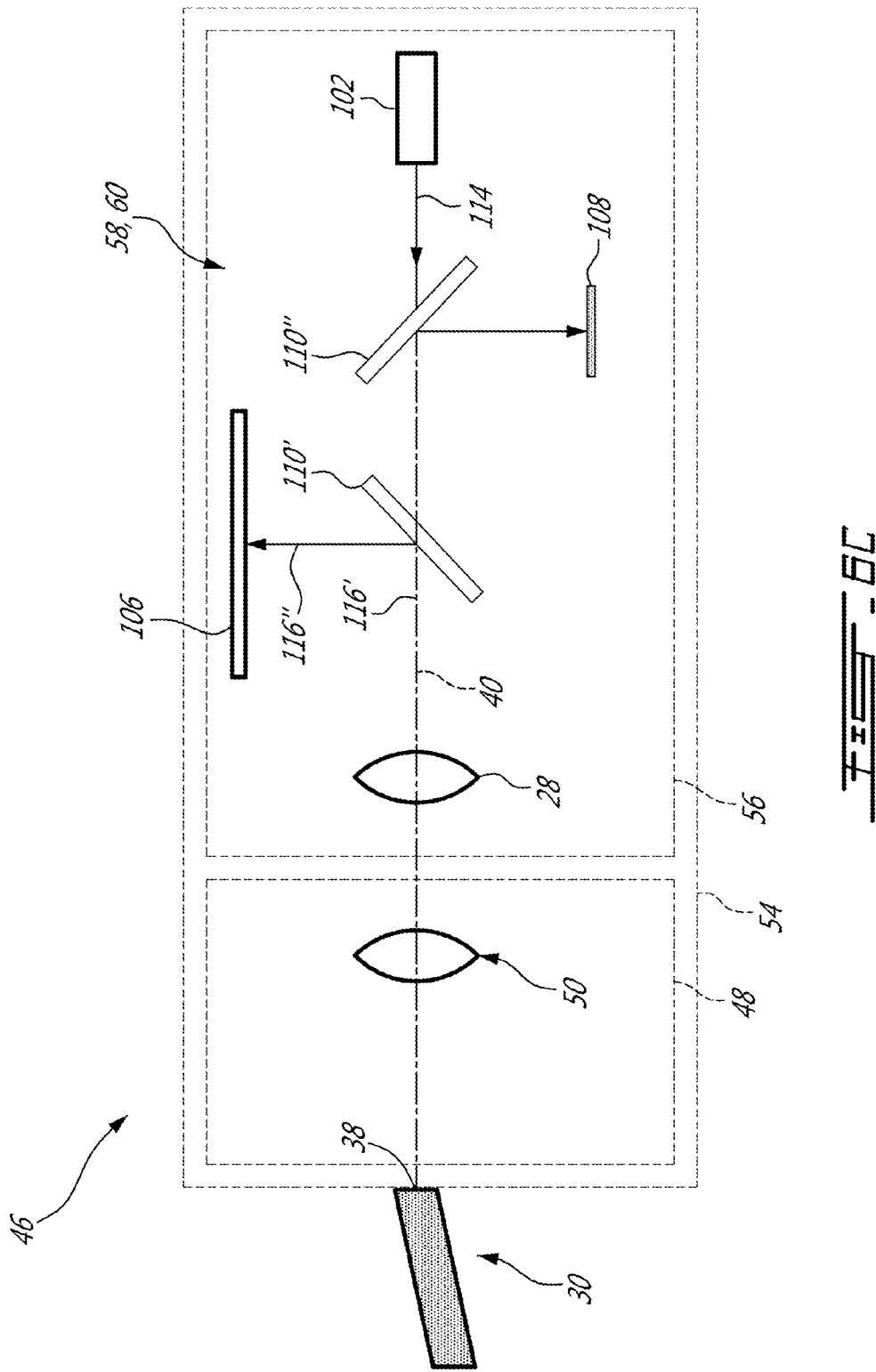

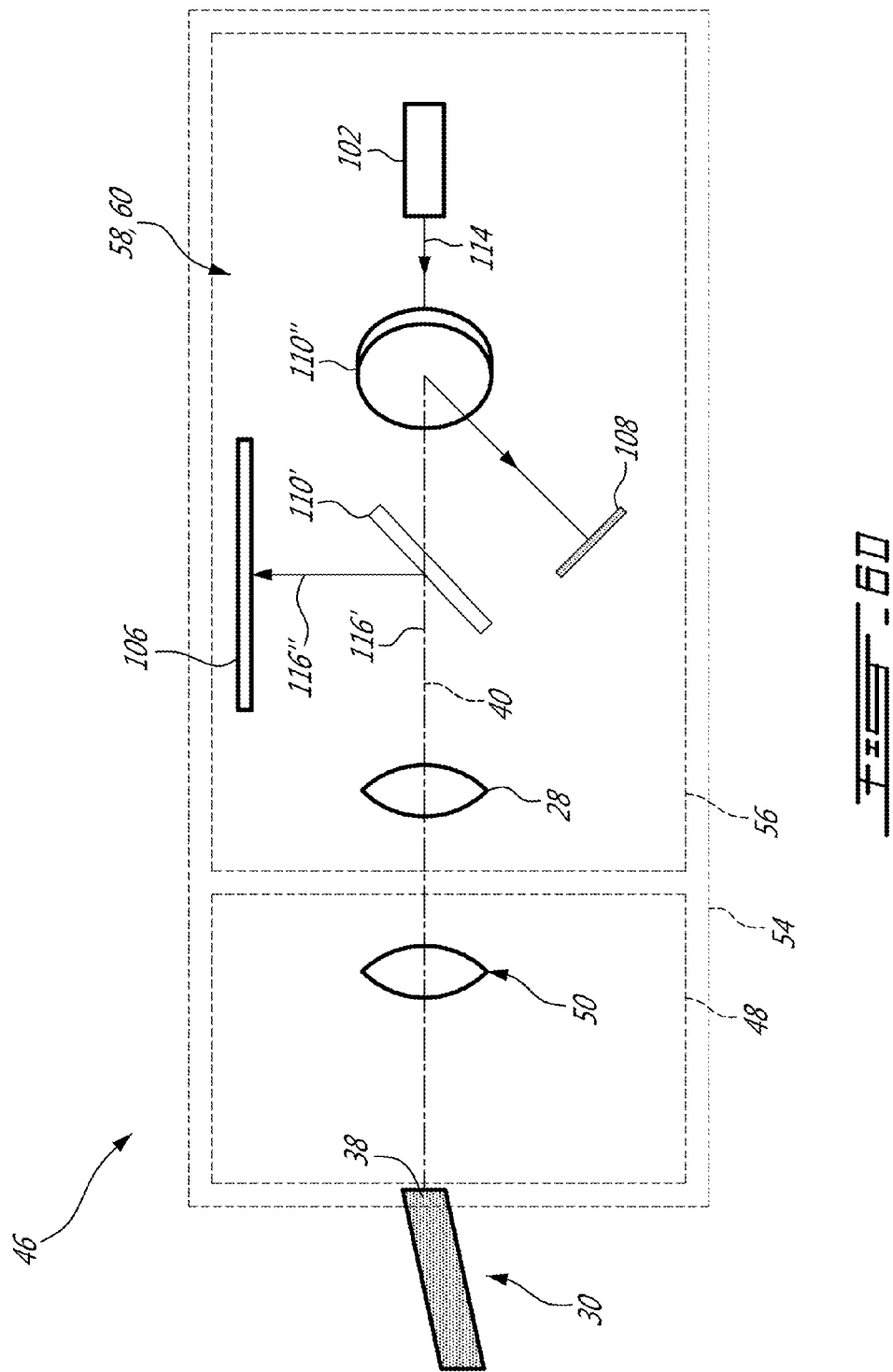

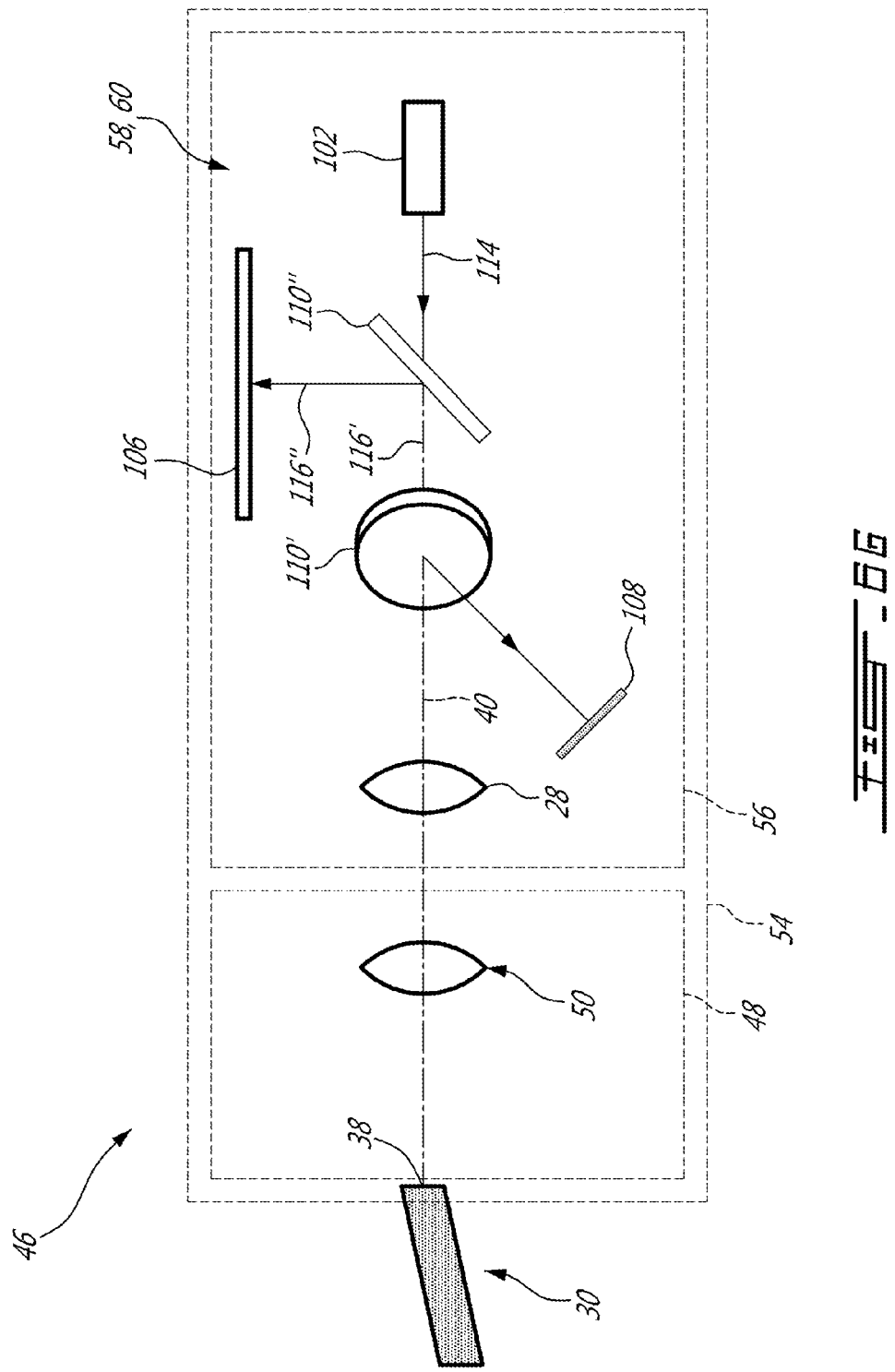

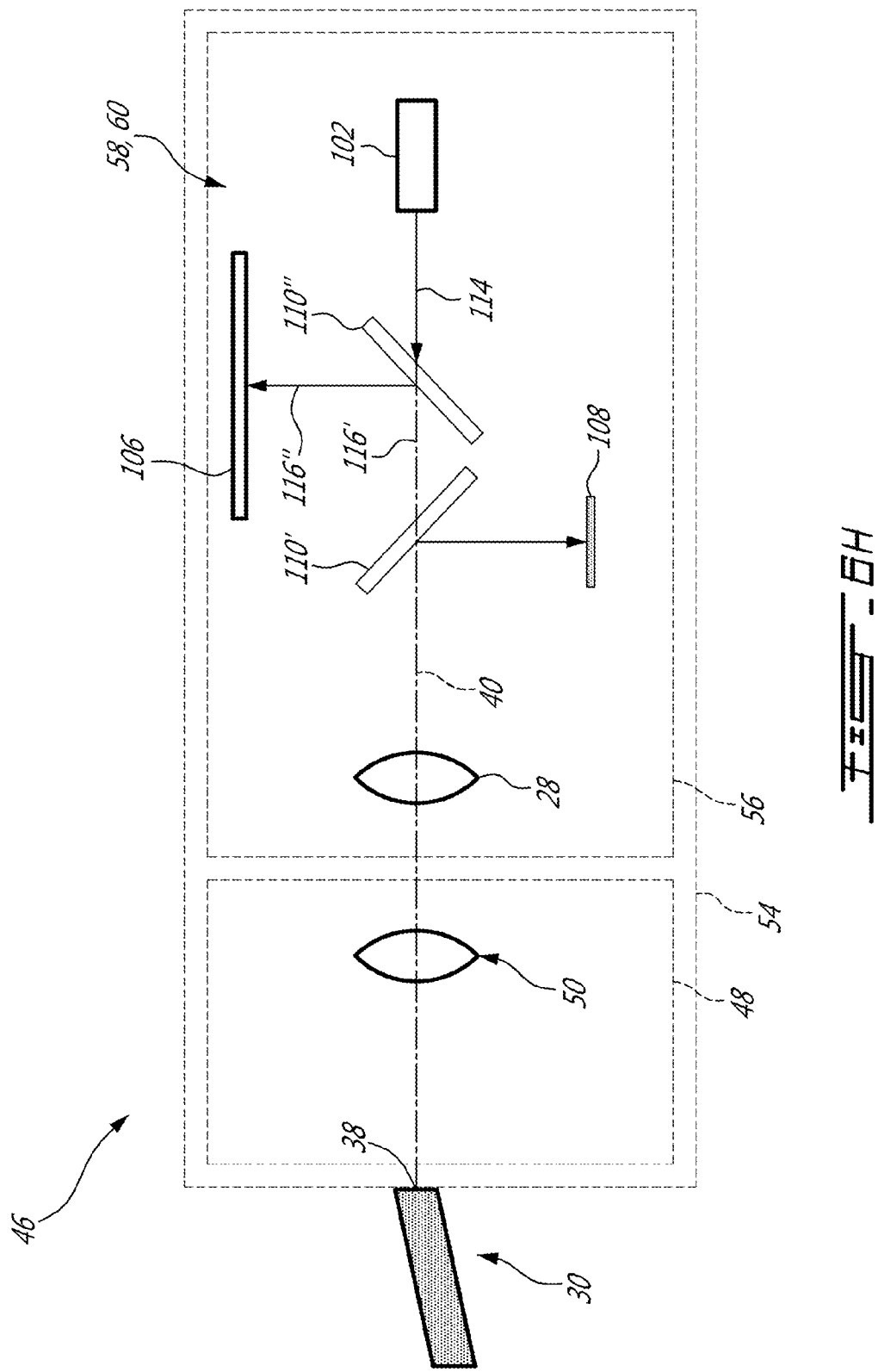

FIBER INSPECTION MICROSCOPE AND POWER MEASUREMENT SYSTEM, FIBER INSPECTION TIP AND METHOD USING SAME

CROSS-REFERENCE TO RELATED APPLICATIONS

This patent application claims priority of U.S. provisional Application Ser. No. 62/091,872, filed on Dec. 15, 2014 and of U.S. provisional Application Ser. No. 62/154,018, filed on Apr. 28, 2015, the contents of which are hereby incorporated by reference.

FIELD

The improvements generally relate to optical-fiber connector inspection, and more particularly, to optical-fiber connector inspection probes having integrated optical power measurement and imaging capabilities.

BACKGROUND

The quality and cleanliness of endfaces of optical-fiber connectors represent important factors for achieving adequate system performance of optical communication networks. Indeed, any contamination of or damage on the mating surface of an optical-fiber connector may severely degrade signal integrity. Optical-fiber connector inspection microscopes are commonly employed to visually inspect the endface of an optical-fiber connector at installation or during maintenance of optical communication networks, in order to verify the quality of the optical-fiber connection.

Some optical-fiber inspection microscope probes also include a separate power detection port which allows the operator to measure the optical power of light exiting the optical-fiber connector. The operator is therefore required to sequentially connect the optical-fiber connector under inspection to the inspection microscope port and to the power detection port. Of course, additional handling of optical-fiber connectors increases the risk of potential contamination of the connector endface.

U.S. Pat. No. 8,908,167 to Flora et al. proposes an optical-fiber inspection microscope configuration that includes an integrated optical power measurement assembly such that visual inspection and power measurement may be conducted using the same port. However, Flora et al. only addresses the optical power measurement of light exiting perpendicularly-polished optical-fiber connectors, for which light is known to exit along the normal of the connector endface.

Although existing optical-fiber inspection microscope probes are satisfactory to a certain degree, there remains room for improvement, particularly in terms of providing a fiber inspection microscope system having integrated optical power measurement, which is configured to inspect angle-polished optical-fiber connectors.

SUMMARY

Accordingly, there is provided a releasable fiber inspection tip to be connected to a fiber inspection microscope and power measurement probe (referred to as "fiber inspection probe"), a fiber inspection microscope and power measurement system (referred to as "fiber inspection system") and a method for both visually inspecting an optical-fiber endface of an angle-polished connector and measuring the optical power of light exiting the optical-fiber connector at the optical-fiber endface.

The mean propagation direction of light exiting an angle-polished connector is known to be tilted relative to the normal of the optical-fiber endface. It is also known that for suitable visual inspection of an optical-fiber connector, the connector should ideally be oriented such that the endface under inspection is normal to the imaging path of the fiber inspection probe. It follows that the mean propagation direction of light exiting the angle-polished connector is tilted relative to the imaging path, and if the imaging path of the inspection probe is not so oriented, a substantial portion of the exiting light may not reach the objective lens of the fiber inspection probe. The provided fiber inspection tip has a converging element which is configured to receive light exiting the endface of the optical-fiber connector. To do so, the converging element is spaced from the endface of the optical fiber to cooperate with a lens diameter of the converging element to increase the numerical aperture of the inspection microscope, which allows reception of at least a substantial portion of the tilted light in order to redirect the tilted light toward an imaging path of the fiber inspection probe to which the inspection tip is mounted. Such redirection enables the fiber inspection system to both image the endface of the angle-polished connector and to detect an optical power value associated with the tilted light. More specifically, said redirection allows the tilted light to be received by the objective lens of the fiber inspection probe comprising a power detection assembly and an optical-fiber endface imaging assembly.

In accordance with another aspect, there is provided a fiber inspection microscope and power measurement system for inspecting an endface of an optical fiber at an angle-polished connector, the endface of the optical fiber being polished at a non-perpendicular angle relative to a propagation axis of the optical fiber, the fiber inspection microscope and power measurement system comprising: a housing structure; a mating interface mounted to the housing structure and configured to receive the angle-polished connector in an inspection position for inspection of the endface, the endface causing a mean propagation direction of light exiting therefrom to be "tilted" (i.e. a line passing from the center of the optical-fiber core and along the centroid of the exiting light distribution is non-colinear) relative to an imaging path of the fiber inspection microscope and power measurement system; a converging element enclosed in the housing structure, a diameter of the converging element and a distance between the converging element and the mating interface being adapted to receive the tilted light from the endface of the optical fiber, the converging element redirecting the tilted light toward the imaging path of the fiber inspection microscope and power measurement system when the angle-polished connector is in the inspection position; and a power detection assembly enclosed in the housing structure and optically coupled to the converging element to detect an optical power value associated with the tilted light redirected by the converging element during use.

In accordance with another aspect, there is provided a fiber inspection tip for use with a fiber inspection microscope and power measurement probe having a power detection assembly and an optical-fiber endface imaging assembly enclosed therein, the fiber inspection tip comprising: a tip housing having a longitudinal axis, a probe end having a probe interface configured to mate with the fiber inspection microscope and power measurement probe, an inspection end having a mating interface configured to receive an endface of an optical fiber at an angle polished connector, and an inner cavity extending along the longitudinal axis between the probe end and the inspection end, the endface of the optical fiber forming a non-perpendicular angle relative to a propagation axis of the optical fiber and causing a mean propagation direction of light exiting the optical fiber at the endface to be tilted relative to an imaging path of the fiber inspection microscope and power measurement probe; and a converging element disposed in the inner cavity of the tip housing, a diameter of the converging element and a distance between the converging element and the mating interface being adapted to receive the tilted light, the converging element redirecting the tilted light toward the imaging path of the fiber inspection microscope and power measurement probe when the fiber inspection tip is mounted to the fiber inspection microscope and power measurement probe and the angle polished connector is received in the mating interface of the fiber inspection tip.

In accordance with another aspect, there is provided a method for inspecting an endface of an optical fiber at an angle-polished connector using a fiber inspection microscope and power measurement system, the method comprising the steps of: receiving light exiting the endface of the optical fiber using a converging element, the mean propagation direction of said light being tilted relative to an imaging path of the fiber inspection microscope and power measurement system; using the converging element, redirecting the received light toward the imaging path of the fiber inspection microscope and power measurement system; and measuring an optical power value associated with the tilted light redirected by the converging element, using an optical power detector of the fiber inspection microscope and power measurement system.

Advantageously, the converging element of the fiber inspection tip can enhance an imaging resolution of the fiber inspection system. Indeed, the converging element gives rise to an image of the endface on an image sensor of the imaging assembly to be magnified in comparison to fiber inspection tips having no converging element. In some cases, the converging element of the fiber inspection tip can provide an imaging resolution below 0.2 µm per pixel, such that, the fiber inspection system can be said to be "high resolution" according to the standard IEC-61300-3-35, ed 2.0, published by the International Electrotechnical Commission (IEC).

It is understood that the term "visual inspection" is meant to encompass, for instance, embodiments in which an image of the endface of the optical-fiber connector is acquired. In this case, the inspection is said to be "visual" since a visual representation of the endface of the optical fiber may be displayed to an end user and/or processed by an image processing software employing, e.g., object recognition. Although such visual inspection is indirect in the sense that it is an image of the endface that is being displayed or processed, it is still referred to herein as "visual".

Many further features and combinations thereof concerning the present improvements will appear to those skilled in the art following a reading of the present disclosure.

DESCRIPTION OF THE FIGURES

In the figures,

FIG. 1A is a schematic cross-sectional view of an example of a fiber inspection probe showing simulated rays propagating from a non-angled polished connector;

FIG. 1B is a schematic cross-sectional view of an example of a fiber inspection probe showing simulated rays propagating from an angle-polished connector;

FIG. 2A is a schematic cross-sectional view of an example of a fiber inspection system showing simulated rays propagating from an angle-polished connector, in accordance with an embodiment;

FIG. 2B is a schematic cross-sectional view of an example of a fiber inspection system showing simulated rays propagating from a non-angled polished connector, in accordance with an embodiment;

FIG. 3A is an oblique view of an example of a fiber inspection system, in accordance with an embodiment;

FIG. 3B is an oblique, fragmented and exploded view of the example of the fiber inspection system illustrated in FIG. 3A;

FIG. 4 is a longitudinal cross-sectional view of a fiber inspection tip for use with a fiber inspection probe, in accordance with an embodiment;

FIG. 5 is an oblique, cross-sectional view of an example of the fiber inspection system shown in FIG. 3A, in accordance with an embodiment;

FIG. 6A is a schematic view of a first example of an optical arrangement of a fiber inspection system including an illumination path having an illumination source and a first beam splitter, a power detection path having a second beam splitter and an optical power detector, and an imaging path having an image sensor, wherein the illumination path and the power detection path are in different planes, and wherein the first beam splitter is closer to a tip housing than the second beam splitter which is itself closer to the tip housing than the image sensor;

FIG. 6B is a schematic view of a second example of an optical arrangement of a fiber inspection system including a power detection path having a first beam splitter and an optical power detector, an illumination path having a second beam splitter and an illumination source, and an imaging path having an image sensor, wherein the power detection path and the illumination path are in different planes, and wherein the first beam splitter is closer to a tip housing than the second beam splitter which is itself closer to the tip housing than the image sensor;

FIG. 6C is a schematic view of a third example of an optical arrangement of a fiber inspection system including an imaging path having a first beam splitter and an image sensor, a power detection path having a second beam splitter and an optical power detector, and an illumination path having an illumination source, wherein the imaging path and the power detection path are in a same plane, and wherein the first beam splitter is closer to a tip housing than the second beam splitter which is itself closer to the tip housing than the illumination source;

FIG. 6D is a schematic view of a fourth example of an optical arrangement of a fiber inspection system including an imaging path having a first beam splitter and an image sensor, a power detection path having a second beam splitter and an optical power detector, and an illumination path having an illumination source, wherein the imaging path and the power detection path are in different planes, and wherein the first beam splitter is closer to a tip housing than the second beam splitter which is itself closer to the tip housing than the illumination source;

FIG. 6G is a schematic view of a seventh example of an optical arrangement of a fiber inspection system including a power detection path having a first beam splitter and an optical power detector, an imaging path having a second beam splitter and an image sensor, and an illumination path having an illumination source, wherein the power detection path and the imaging path are in different planes, and wherein the first beam splitter is closer to a tip housing than the second beam splitter which is itself closer to the tip housing than the illumination source; and FIG. 6H is a schematic view of an eighth example of an optical arrangement of a fiber inspection system including a power detection path having a first beam splitter and an optical power detector, an imaging path having a second beam splitter and an image sensor, and an illumination path having an illumination source, wherein the power detection path and the imaging path are in a same plane, and wherein the first beam splitter is closer to a tip housing than the second beam splitter which is itself closer to the tip housing than the illumination source.

DETAILED DESCRIPTION

Figure 6E:
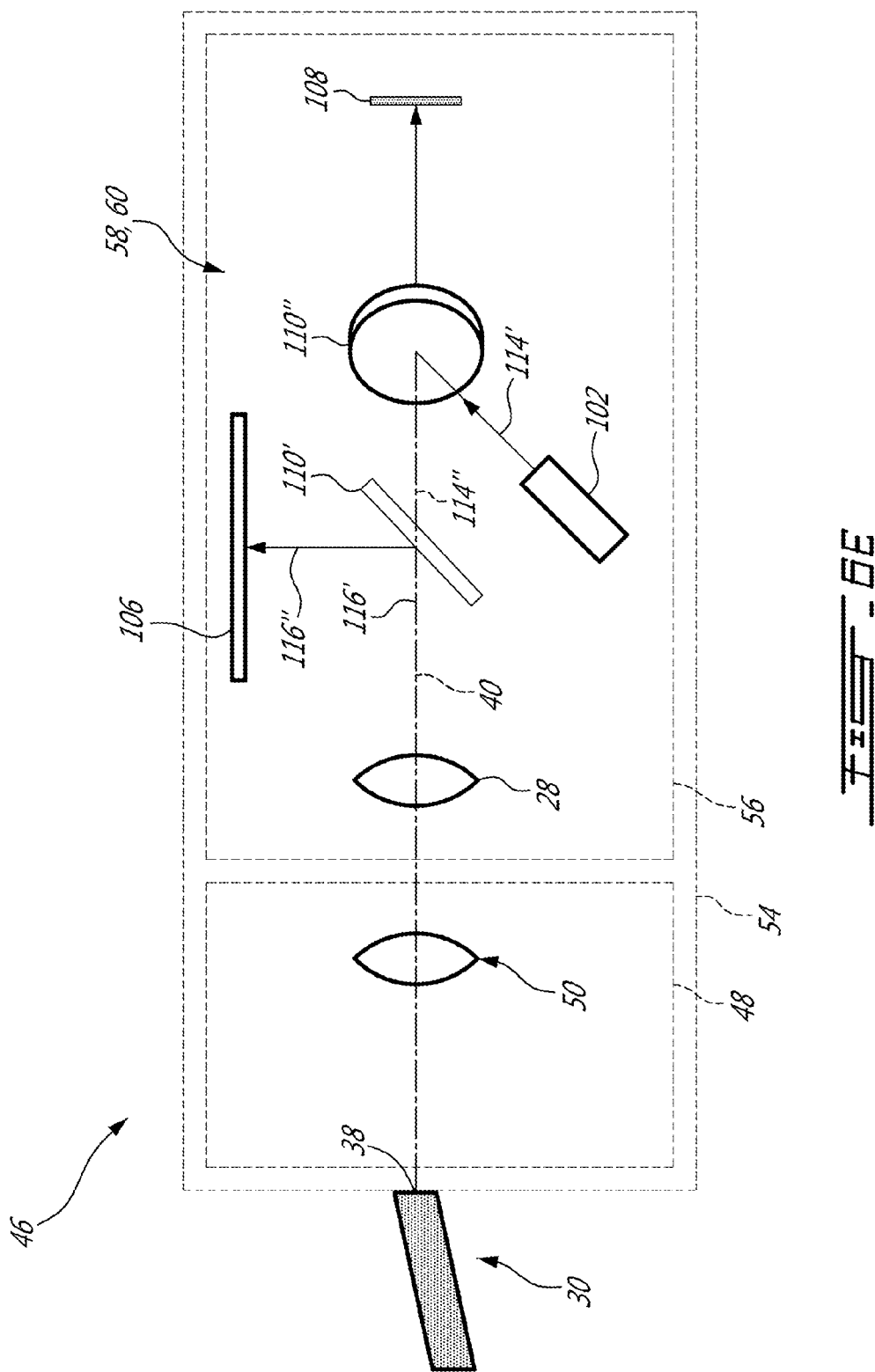
FIG. 6E is a schematic view of a fifth example of an optical arrangement of a fiber inspection system including an imaging path having a first beam splitter and an image sensor, an illumination path having a second beam splitter and an illumination source, and a power detection path having an optical power detector, wherein the imaging path and the illumination path are in different planes, and wherein the first beam splitter is closer to a tip housing than the second beam splitter which is itself closer to the tip housing than the optical power detector.

Optical connectors normally need to be inspected when they are connected and disconnected from one another. Typically, the procedure involves a first step of measuring an optical power value using an optical power detector and a second step of visually inspecting the optical-fiber connector endface using a fiber inspection microscope. However, undesirable particles can be deposited on the endface of the optical fiber while manipulating the optical fiber from the fiber inspection probe to the optical power detector, for instance. To circumvent this drawback, some have proposed fiber inspection probes adapted to inspect endfaces of perpendicularly-polished connectors that would incorporate both an optical-fiber endface imaging assembly and an optical power detection assembly. Such inspection probes would allow performing the two steps mentioned above in a single step, thus reducing the risk of contamination. However, the such fiber inspection probes are not configured to inspect endfaces of angle-polished connectors. The following disclosure describes an inspection tip which, when coupled to a fiber inspection microscope and power measurement probe, allows inspection of connectors having angle-polished endfaces, as well as power measurement.

FIG. 1A shows a schematic side view of an inspection microscope probe 10 having a fiber adaptor tip 12, in accordance with prior art inspection microscope probes. In the depicted case, the fiber adaptor tip 12 is employed to inspect a non-angled polished optical-fiber connector 16 such as a physical-contact ferrule connector (FC/PC). As known in the art, the fiber adapter tip 12 is typically interchangeable with other adapter tips in order to inspect different configurations of optical-fiber connectors such as, e.g., LC/PC, LC/APC, SC/PC, SC/APC or FC/APC connectors as known in the art. The non-angled polished connector 16 typically has a ferrule end (not shown) that is perpendicular to the propagation axis 22 of the optical fiber 14. The endface of the non-angled polished optical-fiber connector 16 coincides with the ferrule end such that the endface of the optical fiber 14 causes light propagating in the optical fiber 14 to exit the connector endface in a diverging light beam of which the mean propagation direction is perpendicular to the connector endface (i.e. in continuity with the propagation axis 22 of the optical fiber 14).

As depicted in FIG. 1A, the non-angled polished connector 16 is mated to the fiber adaptor tip 12, which is, in turn, mated to the fiber inspection probe 10. When the non-angled polished connector 16 is mated to the fiber inspection probe 10, a conventional spacing distance 26 separates the flat endface and an objective lens 28. A light beam, which diverges from the non-angled polished endface of the optical fiber 14, propagates toward the objective lens 28 of the fiber inspection probe 10.

FIG. 1B shows a schematic side view of the fiber inspection probe 10 on which the fiber adaptor tip has been interchanged with a fiber adaptor tip 12' that is made to receive an angle-polished connector 30 such as, e.g. an angle-polished physical-contact ferrule connector (FC/APC connector). As best shown in insets 32 and 34, the angle-polished connector 30 typically has an angled ferrule end 36 which is not perpendicular to the propagation axis 22 of the optical fiber 14. The angle-polished endface 38 of the optical-fiber connector coincides with the angled ferrule end 36. The fiber adaptor tip 12' has a mating interface which is configured such that the angle-polished endface 38 is perpendicular to an imaging path of the fiber inspection probe 10 in order to suitably image the angle-polished endface 38. In the embodiment shown, the imaging path corresponds to a longitudinal axis 40 of the probe, which will be referred to as the probe axis 40. Also, it is understood that the probe axis 40 may not coincide with the imaging path depending on the design of the fiber inspection probe, for instance. The angle-polished endface 38 (which will be simply referred to as "endface 38" hereinbelow) of the optical fiber 14 causes a mean propagation direction of light 42 exiting the endface 38 to be tilted relative to both the propagation axis 22 of the optical fiber 14 and, more importantly, the probe axis 40 of the fiber inspection probe 10, as shown in FIG. 1B. Consequently, the endface 38 prevents a significant portion of the tilted light 42 from reaching the objective lens 28 of the fiber inspection probe 10, and therefore being captured by the optical system of the fiber inspection probe 10. It will therefore be understood that it is thus not possible in the embodiment of FIG. 1B to measure the optical power of light exiting the optical-fiber endface 38 with the fiber inspection probe 10.

FIG. 2A shows a schematic side view of a fiber inspection microscope and power measurement system 46 (referred to as "fiber inspection system 46"), in accordance with an embodiment. The fiber inspection system 46 is configured for measuring the optical power of light exiting the angle-polished endface 38 (see inset of FIG. 1B) of the angle-polished connector 30. The fiber inspection system 46 comprises a fiber inspection tip 44 and a fiber inspection probe 10. During inspection, the angle-polished connector 30 is mated to the fiber inspection tip 44, which is, in turn, mated to the fiber microscope probe 10. As depicted in this embodiment, the fiber inspection tip 44 has tip housing 48 which encloses a converging element (CE) generally shown at 50. When the fiber inspection tip 44 is in an inspection position, i.e. when the optical fiber 14 is mated to the fiber inspection tip 44 via the angle-polished connector 30 and when the fiber inspection tip 44 is mated to the fiber inspection probe 10, the CE 50 is configured to receive the tilted light 42 and to redirect the tilted light 42 toward the probe axis 40 of the fiber inspection probe 10. More specifically, the CE 50 is configured to redirect the tilted light 42 into the objective lens 28 of the fiber inspection probe 10.

In the inspection position, the CE 50 is characterized by a given lens diameter and by a spacing distance 52 separating the CE 50 from the endface 38 of the optical fiber 14 along the probe axis 40. Indeed, reception of the tilted light 42 is allowed by the spacing distance 52 and the lens diameter of the CE 50. Accordingly, the required lens diameter of the CE 50 reduces proportionally with the spacing distance 52. In other words, the closer the CE 50 is positioned relative to the endface 38 of the optical fiber 14, the lower the required diameter of the CE 50. Consequently, the spacing distance 52 along with the diameter of the CE 50 is specifically chosen to ensure that a significant portion of the tilted light 42 is received and redirected toward the probe axis 40 of the fiber inspection probe 10. In some embodiments, the spacing distance 52 can be between 5 mm and 8 mm and preferably between 6 mm and 7 mm, while the diameter of the CE 50 is greater than 2 mm and preferably greater than 5 mm. Using the CE 50, the numerical aperture of the fiber inspection system is increased to about 0.31 or above.

FIG. 2B shows a schematic side view of the fiber inspection system 46 having a fiber inspection tip 44', in accordance with an embodiment. As illustrated, the CE 50 is also configured to receive light exiting the optical fiber 14 at the non-angled polished connector 16. Accordingly, the fiber inspection tip 44' and the fiber inspection system 46 can be used with non-angled polished connectors, such as connector 16. Advantageously, it was found that the use of the CE 50 of the fiber inspection tips 44, 44' can enhance an imaging resolution of the fiber inspection system 46 due to their generally magnifying nature. Indeed, the converging element causes an image of the endface on an image sensor of the imaging assembly to be magnified compared to fiber adaptor tips having no CE, such as adaptor tips 12 and 12'. It can be possible to obtain an imaging resolution below 0.2 μm per pixel, which can be said to be "high resolution" according to the standard IEC-61300-3-35, ed. 2.0, published by the International Electrotechnical Commission (IEC). It was found that the use of the CE could reduce a field of view of the image sensor. However, imaging the non-angled polished connector 16 or the angle-polished connector 30 with a high resolution imaging can be possible by providing the fiber inspection system 46 with satisfactory mechanical tolerances and/or by providing the image sensor with a satisfactory detection surface.

Advantageously, in use, an operator of the fiber inspection system 46 may readily interchange regular tips, such as tip 12 or 12', with high-resolution tips, such as tip 44 or 44' in order to obtain a higher resolution when needed, and this with only a small downside on the reduction of the field of view of the fiber inspection system 46. It will be understood that an APC-adapted power measurement tip that includes a CE (such as tip 44) should be employed for applications in which the optical power of an angle-polished connector is to be measured with the fiber inspection system 46.

FIG. 3A shows an oblique view of the fiber inspection system 46, in accordance with an embodiment. The fiber inspection system 46 has a housing structure 54 including the tip housing 48 and a probe housing 56 which allow the fiber inspection tip 44 to be releasably connectable to the fiber inspection probe 10. Accordingly, an operator using the fiber inspection probe 10 can select an appropriate one of the fiber inspection tips, e.g. 44 or 44', corresponding to the connector to be inspected. In the embodiment shown, the housing structure 54 has a generally narrow and elongated front portion, which can be useful when inspecting a patch panel including a matrix of closely spaced angle-polished connectors 30.

It is understood that the tip housing 48 encloses the CE 50 whereas the probe housing 56 encloses an optical-fiber endface imaging assembly 58 (referred to as "imaging assembly 58") for imaging the endface 38 of the optical fiber 14 when the angle-polished connector 30 is in the inspection position, and a power detection assembly 60 for measuring an optical power value associated to at least a portion of the tilted light 42, for instance. As will be described hereinbelow, FIGS. 5-6H show different exemplary configurations of the imaging assembly 58 and the power detection assembly 60.

As shown in the exploded view of a portion of the fiber inspection system 46 depicted in FIG. 3B, the tip housing 48 has a generally cylindrical body defining a longitudinal axis, an inspection end 64 and a probe-connecting end 66. More specifically, the tip housing 48 has a first cylindrical portion 68 having a first external diameter, a second frustoconical portion 70 extending from the first external diameter to a second, larger external diameter, and a third cylindrical portion 72 having the second external diameter, for instance. In other embodiments, the tip housing 48 can have other shapes as deemed suitable.

Moreover, the inspection end 64 has a mating interface 74 for receiving the angle-polished connector 30. In this embodiment, the mating interface 74 is embodied by a tubular body having first internal dimensions complementary to external dimensions of the ferrule 36 of the angle-polished connector 30, for snugly receiving to the ferrule 36. It is contemplated that the mating interface 74 can be modified as known in the art to inspect the angle-polished connector 30 via a bulkhead adapter (not shown) and the like.

Still referring to FIG. 3B, the probe-connecting end 66 of the fiber inspection tip 44 has a probe interface 78 which comprises a screw-threaded mechanism embodied by threads on the external surface of the third cylindrical portion 72 of the tip housing 48 (threads not apparent in FIG. 3B) for securing to internally-threaded swiveled ring 80 on the fiber inspection probe 10, for instance. In the embodiment of FIG. 3B, the probe-connecting end 66 has a first alignment channel 86 (a notch) recessed axially from the probe-connecting end 66. The first alignment channel 86 is configured to receive an inspection tip alignment key (not shown) of the fiber inspection probe 10 in order to align the fiber inspection tip 44 appropriately relative to the fiber inspection probe 10. In an embodiment, the fiber inspection tip 44 has a visual alignment indicator 85 on the third cylindrical portion 72 of the tip housing 48. In use, an operator positions the angle-polished connector 30 in the inspection tip 44 such that a connector alignment key 84 (as shown in FIG. 4) of the angle-polished connector 30 is suitably aligned with the visual alignment indicator 85. In the embodiment shown, the visual alignment indicator 85 is a channel recessed axially along the third cylindrical portion 72 of the tip housing 48. In the embodiment shown, the tip housing 48 has an inner surface defining an inner cavity 88 (shown in FIG. 4) which encloses the CE 50, and a retaining ring 90 for maintaining the CE 50 at a desired location in the inner cavity 88, as further described hereinbelow.

FIG. 4 is a cross-sectional view of the fiber inspection tip 44 illustrated along with the angle-polished connector 30 (shown in a schematic side view). As depicted, the tip housing 48 encloses the CE 50 which is embodied by a converging compound lens 92 in this exemplary embodiment. In this specific embodiment, the converging compound lens 92 includes a positive meniscus lens 94 and a bi-convex lens 96 serially disposed next to one another, wherein the bi-convex lens 96 is adjacent to the probe-connecting end 66 of the fiber inspection tip 44, for instance. Of course, other converging lens systems 92 can be used. For example, in another embodiment, the CE 50 is a simple converging lens. The CE 50 can be inserted into the inner cavity 88 via an open end 98 of the inner cavity 88, toward the probe-connecting end 66. The inner cavity 88 has inner radial dimensions that closely fit that of the CE 50 so as to properly align the CE 50 within the fiber inspection tip 44. The CE 50 is held axially by the retaining ring 90 against a stopper 87 on the inner surface of the third cylindrical portion 72 of the inspection tip 44. The retaining ring 90 has threads 93 on an outer surface thereof which are secured in corresponding threads 95 of the inner surface of the third cylindrical portion 72.

It is to be noted that the tubular body of the mating interface 74 defines a ferrule receiving channel 100 that is tilted relative to the probe axis 40 of the fiber inspection probe 10 so that the angle-polished endface 38 of the optical fiber 14 is perpendicular to the imaging path of the fiber inspection probe 10 when the angle-polished connector 30 is in the inspection position. In the embodiment shown, the first cylindrical portion 68 is tilted relative to the third cylindrical portion 72.

As mentioned above, FIGS. 5-6H show exemplary configurations of the imaging assembly 58 and the power detection assembly 60 which may be used to, respectively, image the endface 38 of the optical fiber 14 and measure an optical power value associated with the tilted light 42 exiting the optical fiber 14 at the endface 38. The configuration of the imaging assembly 58 and of the power detection assembly 60 are not limited to those presented herein, but can encompass any suitable configuration. In the following, similar elements present in FIGS. 5-6H are not repetitively described for ease of reading.

As understood by one skilled in the art, the imaging assembly 58 includes an illumination source 102 for illuminating the endface 38 of the optical fiber 14 and imaging optics, including the objective lens 28 (and optionally other lenses or mirrors), for imaging the illuminated endface 38 on an image plane 104 coinciding with an image sensor 106. Moreover, the power detection assembly 60 comprises an optical power detector 108 for measuring the optical power value of light exiting the optical fiber 14 at the endface 38.

Separating optics, such as coated or uncoated optical plates, are positioned along the probe axis 40 of the fiber inspection probe 10 to redirect light to any desired location within the inspection microscope probe 10. In the embodiments shown, the separating optics are embodied by beam splitters 110', 110". The beam splitters 110', 110" are preferably 50/50 power beam splitters which separate light into two similar light beams. Indeed, the separating optics can be used to reflect illumination light transmitted from the illumination source 102 along the probe axis 40 and toward the endface 38 of the optical fiber 14. Also, the separating optics can be used to apportion an imaging beam from a signal beam and to direct the imaging beam and the signal beam to, respectively, the image sensor 106 and the optical power detector 108. As defined herein, the imaging beam is the light beam caused by the reflection of the illumination light on the endface 38 of the optical fiber 14 and which is in the field of view of the image sensor 106, and the signal beam corresponds to light exiting the optical fiber 14 at the endface 38.

Typically, the illumination beam has a short wavelength in order to enhance the imaging resolution (since the diffraction limit is proportional to the wavelength) while keeping a wavelength that can be measured using commercially available image sensors 106 which are both cost- and size-accessible, such as a complementary metal-oxide-semiconductor (CMOS) sensor or a charge-coupled device (CCD), for instance. The illumination source 102 can be embodied in a light-emitting diode (LED) emitting in the blue region, e.g. at about 470 nm. Indeed, such a blue light allows for an acceptable imaging resolution while being easily measured using conventional CMOS sensors or CCDs. However, other illumination sources 102 can be found suitable depending on the circumstances.

The fiber inspection system 46 can be designed to operate either in a simultaneous manner or in a sequential manner. If operated in the simultaneous manner, imaging of the illuminated endface 38 and optical power measurement are performed at the same time. As may be apparent to one skilled in the art, simultaneous measurements require the separating optics to be dichroic (by use of a dichroic coating). Indeed, in this case, dichroic beam splitters can separate light associated with the optical telecommunication range (e.g. 700 nm to 1675 nm) from light associated with the illumination range (e.g. 380 nm to 700 nm) at all times so as to avoid stray portions of the imaging beam giving rise to bias in the optical power measurement of the signal beam, for instance. If operated in a sequential manner, the imaging of the illuminated endface 38 is performed prior to or after the optical power measurement in a manner that does not necessitate the separating optics to have dichroic coating deposited thereon. In other words, the illumination source is shut off so that there is no illumination while measuring the optical power value associated with the tilted light 42. It should be noted that anti-reflection coatings can be required irrespective of the manner of operation, i.e. simultaneous or sequential.

It is understood that the spectral content of the imaging beam and of the signal beam can vary depending on commercial applications.

Depending on the configuration of the imaging assembly 58 and of the power detection assembly 60, the disposition of the illumination source 102, the image sensor 106, the optical power detector 108 and the separating optics along the probe axis 40 of the fiber inspection probe 10 may vary, as described herebelow in FIGS. 5-6D.

FIG. 5 shows an oblique view of a longitudinal cross-section of the fiber inspection system 46 shown in FIG. 3A, with the illumination source 102 (shown in block diagram) and the optical power detector 108 shown exploded from the probe housing 56. As illustrated, the imaging assembly has the objective lens 28 which is provided at an end of the probe housing 56. The objective lens 28 images the illuminated endface 38 of the optical fiber 14 (not shown) on the image sensor 106, which is disposed at the opposite portion of the probe housing 56. The imaging beam crosses a first beam splitter 110' and a second beam splitter 110" before reaching the image sensor 106. In this embodiment, the illumination source 102 illuminates the endface 38 via the first beam splitter 110' while the second beam splitter 110" is used to redirect light exiting the optical fiber 14 at the endface 38 for measuring the optical power value with the optical power detector 108.

FIG. 6A shows a schematic view of the fiber inspection system 46 shown in FIGS. 3A and 5. As depicted, the tilted light 42 exits the endface 38 of the angled-polished connector 30 and is directed toward the optical power detector 108 via the CE 50, the objective lens 28 and the first and the second beam splitters 110', 110". In this embodiment, the imaging path 116 of the imaging assembly coincides with the probe axis 40. Correspondingly, in this embodiment, the illumination source 102 projects the illumination light along the illumination path which has a portion 114' between the illumination source 102 and the first beam splitter 110', and another portion 114" between the first beam splitter 110' and the objective lens 28. Moreover, the first beam splitter 110' is at an azimuthally-orthogonal orientation with respect to the second beam splitter 110" (i.e., the orientation of the first beam splitter 110' is that of the second beam splitter 110" rotated by 90 degrees about the probe axis 40) in order to compensate possible aberrations caused by propagation of the imaging beam across the separating optics (i.e. the first and the second beam splitters 110', 110" in this embodiment).

FIG. 6B shows a schematic view of the fiber inspection system 46, in accordance with another embodiment. As depicted, the tilted light 42 exits the endface 38 of the angled-polished connector 30 and is directed toward the optical power detector 108 via the CE 50, the objective lens 28 and the first beam splitter 110'. In this embodiment, the imaging path 116 of the imaging assembly coincides with the probe axis 40. The illumination source 102 illuminates the endface 38 via a reflection on the second beam splitter 110" and a passage through the first beam splitter 110', the objective lens 28 and the CE 50. Also in this embodiment, the first beam splitter 110' is at an azimuthally-orthogonal orientation with respect to the second beam splitter 110" in order to compensate possible aberrations caused by propagation of the imaging beam across the first and the second beam splitters 110', 110".

FIG. 6C shows a schematic view of the fiber inspection system 46, in accordance with another embodiment. As depicted, the angle-polished endface 38 is perpendicular to a first portion 116' of an imaging path of the fiber inspection probe 10. In this embodiment, the tilted light 42 exits the endface 38 of the angled-polished connector 30 and is directed toward the optical power detector 108 via the CE 50, the objective lens 28, the first beam splitter 110', and reflection on the second beam splitter 110" for measuring an optical power value associated with the corresponding light beam. In this specific embodiment, the illumination source 102 is aligned along an illumination path 114 which, in this embodiment, is completely linear. Indeed, the illumination path 114 crosses the second beam splitter 110" and the first beam splitter 110' before reaching the angle-polished endface 38. The imaging beam propagates along the imaging path which has the first portion 116' along the probe axis 40 and a second portion 116" bifurcated by the first beam splitter 110' in order to be imaged on the image sensor 106. Accordingly, the imaging beam is propagated through the objective lens 28 and is then perpendicularly reflected on the image sensor 106 by the first beam splitter 110'. It is to be noted that, in this embodiment, the image of the illuminated endface 38 is free from aberrations that can be caused by propagation across beam splitters, since the image is only reflected by the first beam splitter 110'.

FIG. 6D shows a schematic view of the fiber inspection system 46, in accordance with yet another embodiment. As depicted, this embodiment is similar to the embodiment shown in FIG. 6C but for the second beam splitter 110" that is at an azimuthally-orthogonal orientation with respect to the first beam splitter 110'.

FIG. 6E shows a schematic view of the fiber inspection system 46, in accordance with yet another embodiment. As depicted, the objective lens 28, the first beam splitter 110' and the image sensor 106 are configured in a similar fashion to the embodiment presented in FIG. 6C, which eliminates aberrations that can be caused by propagation of the imaging beam across the second beam splitter 110". However, in this case, the optical power detector 108 and the illumination source 102 are interchanged such that the optical power detector 108 is aligned with the objective lens 28, at an opposite portion of the housing structure 54. Similarly to the embodiment of FIG. 5, the second beam splitter 110" is also at an azimuthally-orthogonal orientation with respect to the first beam splitter 110'.

Figure 6F:
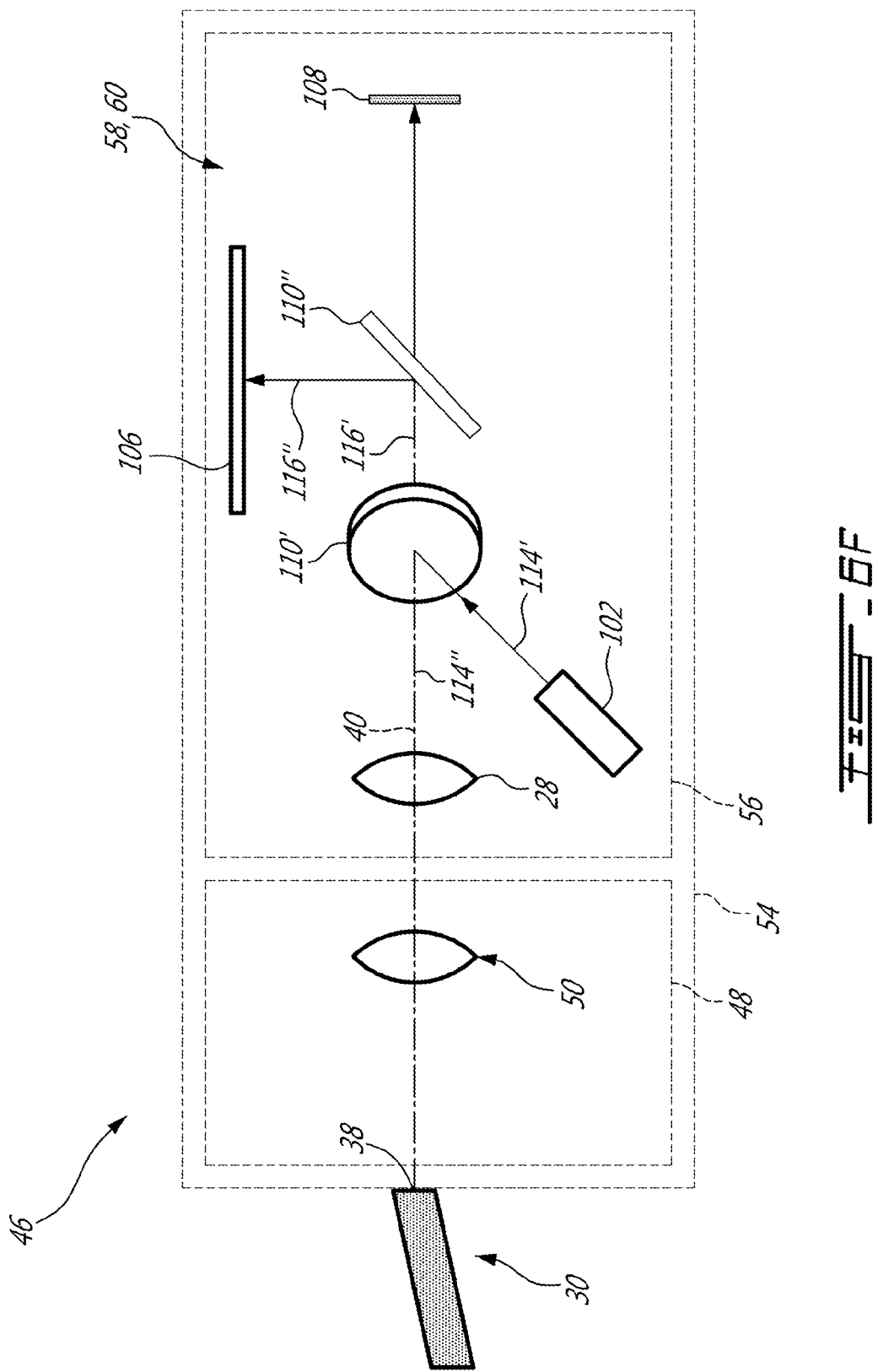
FIG. 6F is a schematic view of a sixth example of an optical arrangement of a fiber inspection system including an illumination path having a first beam splitter and an illumination source, an imaging path having a second beam splitter and an image sensor, and a power detection path having an optical power detector, wherein the illumination path and the imaging path are in different planes, and wherein the first beam splitter is closer to a tip housing than the second beam splitter which is itself closer to the tip housing than the optical power detector.

FIG. 6F shows a schematic view of the fiber inspection system 46, in accordance with still another embodiment. As depicted, light exiting the optical fiber 14 at the angle-polished endface 38 is projected along the probe axis 40 and across the first beam splitter 110' and the second beam splitter 110" before reaching the optical power detector 108, where the measurement of the optical power value is performed. In this embodiment, the first beam splitter 110' is configured to reflect the illumination light from the illumination source 102 in the direction of the angle-polished endface 38 and the second beam splitter 110" to perpendicularly reflect the imaging beam toward the image sensor 106.

FIG. 6G shows a schematic view of the fiber inspection system 46, in accordance with still another embodiment. As depicted, this embodiment is similar to the embodiment shown in FIG. 6F but with the position of the illumination source 102 interchanged with that of the optical power detector 108.

FIG. 6H shows a schematic view of the fiber inspection system 46, in accordance with still another embodiment. As shown, similarly to the embodiment of FIG. 6C, the illumination source 102 is at the opposite portion of the housing structure 54 relative to the angle-polished endface 38. The first beam splitter 110' is configured to reflect light exiting the optical fiber 14 at the endface 38 toward the optical power detector 108. The second beam splitter 110" is configured to reflect the imaging beam propagating from illuminated endface 38 toward the image sensor 106. As can be understood in view of the above, the second beam splitter 110" may impart aberrations upon the image of the illuminated endface 38 that are not compensated by the azimuthally-orthogonal configuration detailed above.

It is noted that although all embodiments illustrated herein include separate optical power detector and image sensor, the optical power detector may well be embodied directly in the image sensor. In this case, an image sensor configured to operate both in the visible and in the near-infrared regions of the electromagnetic spectrum may be used to perform both the optical power detection and the imaging measurements. Such an embodiment may be appropriate in situations where an optical fiber is used to propagate a signal beam having a spectral content at about 850 nm. Accordingly, the use of a separate optical power detector is avoided.

It was found that placing the CE 50 in the fiber inspection tip 44 provided the additional benefit of magnifying the image of the endface 38 on the image sensor 106, which increases the imaging resolution. Indeed, the CE 50 positioned in the fiber inspection tip 44 changes the magnification of the imaging assembly 58. Accordingly, a side effect of the use of the fiber inspection tip 44 is to improve the imaging resolution of the inspection probe 10. The CE 50 of the fiber inspection tip 44 also acts as a magnifying lens which enlarges the image of the endface 38 at the image sensor 106, and thereby increases the resolution of the fiber inspection system 46 from a low-resolution microscope to a high-resolution microscope as defined in the standard IEC-61300-3-35, ed 2.0, published by the IEC. Indeed, it was found that by providing the CE 50 of the fiber inspection tip 44, a resolution below 0.2 µm per pixel can be obtained, which is in compliance with the standard.

As can be understood, the examples described above and illustrated are intended to be exemplary only. For instance, the fiber inspection tip, the fiber inspection system and the method disclosed herein can be used with single-mode optical fibers, as well as multimode optical fibers or multi-fiber (single-mode or multimode) connectors. Moreover, it is noted that the optical axis of the CE is not meant to be strictly concentrically aligned with the probe axis, the optical axis of the CE can be slightly offset and/or tilted relative to the probe axis. For instance, the lens diameter of the CE substantially corresponds to a cross sectional area of the tilted light 42 measured at a position of the CE, along the imaging path. In this embodiment, the optical axis of the CE is positioned offset and/or tilted relative to the probe axis in order to suitably capture the tilted light 42 exiting from the optical fiber. The scope of the invention is intended to be limited solely by the appended claims.

What is claimed is:

1. A fiber inspection microscope and power measurement system for inspecting an endface of an optical fiber at an angle-polished connector, the endface of the optical fiber being polished at a non-perpendicular angle relative to a propagation axis of the optical fiber, the fiber inspection microscope and power measurement system comprising:
   a housing structure;
   a mating interface mounted to the housing structure and configured to receive the angle-polished connector in an inspection position for inspection of the endface, the endface causing a mean propagation direction of light exiting therefrom to be tilted relative to an imaging path of the fiber inspection microscope and power measurement system;
   a converging element enclosed in the housing structure, a diameter of the converging element and a distance between the converging element and the mating interface being adapted to receive the tilted light from the endface of the optical fiber, the converging element redirecting the tilted light toward the imaging path of the fiber inspection microscope and power measurement system when the angle-polished connector is in the inspection position; and
   a power detection assembly enclosed in the housing structure and optically coupled to the converging element to detect an optical power value associated with the tilted light redirected by the converging element during use.

2. The fiber inspection microscope and power measurement system of claim 1, wherein the converging element is a converging lens system.

3. The fiber inspection microscope and power measurement system of claim 1, wherein a value of a distance between the converging element and the mating interface along the imaging path is between 5 mm and 8 mm.

4. The fiber inspection microscope and power measurement system of claim 1, wherein the fiber inspection microscope and power measurement system comprises a fiber inspection tip having a tip housing and comprising the mating interface and the converging element enclosed in the tip housing; and wherein the housing structure comprises the tip housing and a probe housing enclosing the power detection assembly and an optical-fiber endface imaging assembly.

5. The fiber inspection microscope and power measurement system of claim 4, wherein the imaging assembly is optically coupled to the converging element, the imaging assembly being configured to illuminate the endface of the optical fiber and to image the illuminated endface for inspection thereof, the converging element being configured to redirect the tilted light into an objective lens of the imaging assembly located in the probe housing.

6. The fiber inspection microscope and power measurement system of claim 4, wherein the tip housing has a ferrule receiving channel for receiving the angle-polished connector, the ferrule receiving channel being tilted relative to the imaging path such that the endface of the optical fiber is positioned perpendicularly to the imaging path of the fiber inspection microscope and power measurement system.

7. The fiber inspection microscope and power measurement system of claim 4, wherein a numerical aperture of the imaging assembly is greater than 0.31.

8. The fiber inspection microscope and power measurement system of claim 4, wherein the tip housing is releasably connectable to the probe housing.

9. The fiber inspection microscope and power measurement system of claim 8, wherein the fiber inspection tip is interchangeable with fiber inspection tips having no converging element.

10. The fiber inspection microscope and power measurement system of claim 9, wherein the converging element causes an image of the endface on an image sensor of the imaging assembly to be magnified compared to the fiber inspection tips having no converging element, to obtain a resolution below 0.2 µm per pixel.

11. A fiber inspection tip for use with a fiber inspection microscope and power measurement probe having a power detection assembly and an optical-fiber endface imaging assembly enclosed therein, the fiber inspection tip comprising:
   a tip housing having a longitudinal axis, a probe end having a probe interface configured to mate with the fiber inspection microscope and power measurement probe, an inspection end having a mating interface configured to receive an endface of an optical fiber at an angle-polished connector, and an inner cavity extending along the longitudinal axis between the probe end and the inspection end, the endface of the optical fiber forming a non-perpendicular angle relative to a propagation axis of the optical fiber and causing a mean propagation direction of light exiting the optical fiber at the endface to be tilted relative to an imaging path of the fiber inspection microscope and power measurement probe; and
   a converging element disposed in the inner cavity of the tip housing, a diameter of the converging element and a distance between the converging element and the mating interface being adapted to receive the tilted light, the converging element redirecting the tilted light toward the imaging path of the fiber inspection microscope and power measurement probe when the fiber inspection tip is mounted to the fiber inspection microscope and power measurement probe and the angle-polished connector is received in the mating interface of the fiber inspection tip.

12. The fiber inspection tip of claim 11, wherein the inner cavity is open at the probe end for receiving the converging element.

13. The fiber inspection tip of claim 11, wherein the tip housing has a ferrule receiving channel for receiving the angle-polished connector, the ferrule receiving channel being tilted relative to the imaging path such that the endface of the optical fiber is positioned perpendicularly to the imaging path of the fiber inspection microscope and power measurement probe.

14. The fiber inspection tip of claim 11, wherein the converging element has a lens diameter being greater than 2 mm.

15. The fiber inspection tip of claim 11, wherein a value of a distance between the converging element and the mating interface along the imaging path is between 5 mm and 8 mm.

16. The fiber inspection tip of claim 11, wherein the converging element is a converging lens system.

17. The fiber inspection tip of claim 11, wherein the fiber inspection tip is releasably connectable to the fiber inspection microscope and power measurement probe.

18. The fiber inspection tip of claim 17, wherein the fiber inspection tip is interchangeable with fiber inspection tips having no converging element.

\* \* \* \* \*